(12) United States Patent
Crowl

(10) Patent No.: US 12,151,205 B2
(45) Date of Patent: Nov. 26, 2024

(54) HYDROCARBON RECLAMATOR

(71) Applicant: Joshua Lee Crowl, Boise, ID (US)

(72) Inventor: Joshua Lee Crowl, Boise, ID (US)

(*) Notice: Subject to any disclaimer, the term of this patent is extended or adjusted under 35 U.S.C. 154(b) by 387 days.

(21) Appl. No.: 17/867,639

(22) Filed: Jul. 18, 2022

(65) Prior Publication Data

US 2023/0020768 A1 Jan. 19, 2023

Related U.S. Application Data

(60) Provisional application No. 63/222,876, filed on Jul. 16, 2021.

(51) Int. Cl.
| | | |
|---|---|---|
| *B01D 53/94* | (2006.01) | |
| *C07C 1/04* | (2006.01) | |
| *F01N 3/08* | (2006.01) | |
| *F01N 3/28* | (2006.01) | |
| *F02C 3/34* | (2006.01) | |

(52) U.S. Cl.
CPC .............. *B01D 53/94* (2013.01); *C07C 1/041* (2013.01); *F01N 3/0892* (2013.01); *F01N 3/2803* (2013.01); *F02C 3/34* (2013.01); *B01D 2255/1021* (2013.01); *B01D 2255/1026* (2013.01); *B01D 2255/20738* (2013.01); *B01D 2255/20753* (2013.01); *F01N 2240/05* (2013.01); *F01N 2370/02* (2013.01); *F01N 2510/06* (2013.01); *F01N 2610/04* (2013.01); *F05D 2240/51* (2013.01)

(58) Field of Classification Search
CPC ............ B01D 53/94; B01D 2255/1021; B01D 2255/1026; B01D 2255/20738; B01D 2255/20753; C07C 1/041; F01N 3/0892; F01N 3/2803; F01N 2240/05; F01N 2370/02; F01N 2510/06; F01N 2610/04; F02C 3/34; F05D 2240/51

See application file for complete search history.

(56) References Cited

U.S. PATENT DOCUMENTS

| | | | |
|---|---|---|---|
| 8,413,433 B2* | 4/2013 | Lupescu ................. | F02M 26/35 60/299 |
| 2014/0026558 A1* | 1/2014 | Heuvel ..................... | F01N 5/04 60/273 |
| 2014/0103761 A1* | 4/2014 | Atkins ................. | H02K 7/1815 310/74 |

* cited by examiner

*Primary Examiner* — Audrey B. Walter
(74) *Attorney, Agent, or Firm* — Burdick Patents, P.A.; Sean D. Burdick

(57) ABSTRACT

A hydrocarbon reclamator consists of a closed chamber having an exhaust inlet port, a hydrogen inlet port, and a hydrocarbon outlet port. A magnetic flux is generated at the base of the closed chamber and a rotor is suspended by the magnetic flux within the closed chamber. The rotor is formed as a Tesla turbine having axially spaced discs concentrically mounted on a central shaft, a catalyst is formed on surfaces of the discs, and flow holes are formed through the discs. Venturi forces direct gas to release kinetic energy against the discs, so that hydrogen entering the chamber combines with carbon entering the chamber to form a hydrocarbon that exits the chamber via the hydrocarbon outlet port.

20 Claims, 4 Drawing Sheets

HYDROCARBON RECLAMATOR

RELATED APPLICATIONS

This application claims priority to U.S. Provisional Application 63/222,876 that was filed on Jul. 16, 2021, and which is fully incorporated herein by reference.

BACKGROUND OF THE INVENTION

Field of the Invention

The present invention relates generally to emissions systems for power generation systems that burn hydrocarbon fuels, more specifically to a system for reclaiming unburnt hydrocarbons from such emissions systems, and most specifically to reclaiming unburnt hydrocarbons from engine emissions for recirculation to the engine intake.

Description of Related Art

Carbon has been said to provide the ultimate building blocks of matter. Carbon can be found playing a vital role in all known bio-mechanical processes, primarily a result of carbon's ability to create complex geometrically stable molecular configurations. The very hydrocarbons we draw from the ground to burn daily contain the accumulation of millions of years of potential biochemical energy, arranged in long chemical chains of hydrogen and carbon atoms called alkanes. These alkane hydrocarbons were generated by living cells undergoing a process of energy storage and use. Biology has managed to preserve this energy for so long because of the unique ability for carbon to bind to other atoms to form more complex structures. In biology this is best examined by observing photosynthesis. The plants capture potential energy from the sun, convert it to carbohydrates, animals eat the plants, and the cycle of entropy and energy in motion continues.

Well-known examples of byproducts of these natural processes are hydrocarbon fuels such as coal and oil that are mined from the earth. Energy is derived from these sources by burning the fuels in modern power plants, or by further refinement into gasoline or diesel fuel that can be burned in an internal combustion engine to convert the chemical energy into kinetic energy. The efficiency of internal combustion engines, however, generally ranges between 20 to 40 percent. Much of the energy is lost during the conversion due to factors such as the expansion ratio, friction, excessive fuel-to-air ratio, etc. Some of the energy lost is emitted from the exhaust manifold in the form of unburnt hydrocarbons, unused heat, and kinetic energy of the exhaust gas. There is an unfulfilled need for a high efficiency system for the recovery of kinetic energy stored within the expanding exhaust from an internal combustion engine. Current exhaust systems allow for otherwise unused energy to be lost to the atmosphere.

What is needed is a way to reclaim unused energy from hydrocarbon-based power generation to improve overall efficiency.

SUMMARY OF THE INVENTION

The present invention captures carbon byproduct from hydrocarbon emissions and recycles it through a chemical process that preserves the potential energy required to stabilize the carbon with hydrogen, thus creating alkane molecules. According to the invention, a system capable of producing these synthetic alkane molecules is designed so that the kinetic energy input into the system is not lost through friction or static resistance. The system also promotes ionization of the exhausted atmosphere to strip electrons from carbon dioxide that is present, creating an affinity for the carbon dioxide to react with the introduced hydrogen. This affinity between hydrogen and carbon results in a binding reaction when both elements are introduced to a catalytic metal. These reactions are known as the Fischer-Tropsch process and the Sabatier reaction, which can be used to produce hydrocarbons. Frictionless motion and ionization can both be achieved through the proper arrangement of electromagnetic induction and the presence of a functional diamagnetic structure to provide flux stability. Flux stability avoids generation of heat, and thus energy loss, and in addition discourages free-floating mechanisms from wobbling while suspended in the flux field.

In one embodiment, the present invention provides a system for hydrocarbon reclamation, or equivalently, a hydrocarbon reclamator. The hydrocarbon reclamator includes a closed chamber having an exhaust inlet port, a hydrogen inlet port, and a hydrocarbon outlet port. The hydrocarbon reclamator also includes a means, such as electrical coils, for generating a magnetic flux at the base of the closed chamber, and a rotor suspended by the magnetic flux within the closed chamber. The rotor has a surface having a catalyst, and the rotor is configured to direct gas from the inlet ports to the outlet port. In operation, hydrogen entering the closed chamber via the hydrogen inlet port combines with carbon entering the chamber via the exhaust inlet port to form a hydrocarbon that exits the closed chamber via the hydrocarbon outlet port.

In more elaborate embodiments of the invention, the foregoing hydrocarbon reclamator may include many additional features. For example, the hydrocarbon reclamator may include a primary magnetic flux gear affixed atop the rotor, and the primary magnetic flux gear may optionally include one or more gear teeth comprising a permanent magnet. In addition, the hydrocarbon reclamator may further include secondary magnetic flux gears that are magnetically coupled to the primary magnetic flux gear, and one or more of the secondary magnetic flux gears may be configured to generate electrical current in response to rotation of the primary magnetic flux gear.

In other embodiments, in any of the foregoing hydrocarbon reclamators the rotor may be configured as a Tesla turbine, to generate electrical current in response to exhaust gas entering the exhaust inlet port. The Tesla turbine may be configured as a plurality of rotor discs, and the catalyst may be formed on surfaces of the rotor discs. In various embodiments, the catalyst may be a metal such ruthenium, platinum, nickel, or iron that is plated onto the surface of the rotor. Further, each of the rotor discs defines flow holes configured to direct gas from the inlet ports to the outlet port. Optionally, a rotor disc may be formed from a material having diamagnetic properties. In other embodiments, any of the foregoing hydrocarbon reclamators may be configured so that a base of portion of the rotor comprises a permanent magnet.

Any of the foregoing hydrocarbon reclamators may also be configured to generate hydrocarbons by the Fischer-Tropsch process, and may further include an electrolysis subsystem configured to generate and deliver hydrogen to the hydrogen inlet port. In one embodiment, the electrolysis subsystem is configured to generate and deliver the hydrogen to the hydrogen inlet port. In another embodiment, the electrolysis subsystem is electrically powered by the electrical current generated by the rotor. In another embodiment, the means for generating a magnetic flux at the base of the closed chamber is electrically powered by the electrical current generated by the rotor. In another embodiment, the exhaust inlet port and the hydrocarbon outlet port are in fluid communication with a combustion chamber of an internal combustion engine.

In another embodiment of the invention, a hydrocarbon reclamator as described above includes a Tesla turbine having a plurality of discs concentrically mounted on a central shaft of the rotor and spaced apart axially along the shaft. The rotor is configured so that gasses entering the chamber via the exhaust inlet port travel toward a center of the rotor due to venturi forces to release kinetic energy against one or more of the discs.

BRIEF DESCRIPTION OF THE DRAWINGS

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims. Component parts shown in the drawings are not necessarily to scale, and may be exaggerated to better illustrate the important features of the invention. Dimensions shown are exemplary only. In the drawings, like reference numerals may designate like parts throughout the different views, wherein:

DETAILED DESCRIPTION OF THE INVENTION

The following disclosure presents exemplary embodiments for a hydrogen reclamation system, or equivalently, a hydrogen reclamator, constructed according to the principles of the present invention. The hydrogen reclamator captures carbon byproduct from hydrocarbon emissions and recycles it through a chemical process that preserves the potential energy required to stabilize the carbon with hydrogen, thus creating alkane molecules. According to the invention, a system capable of producing these synthetic alkane molecules is designed so that the kinetic energy input into the system is not lost through friction or static resistance. The system also promotes ionization of the exhausted atmosphere to strip electrons from carbon dioxide that is present, creating an affinity for the carbon dioxide to react with the introduced hydrogen. This affinity between hydrogen and carbon results in a binding reaction when both elements are introduced to a catalytic metal. These reactions are known as the Fischer-Tropsch process and the Sabatier reaction, which can be used to produce hydrocarbons. Frictionless motion and ionization can both be achieved through the proper arrangement of electromagnetic induction and the presence of a functional diamagnetic structure to provide flux stability. Flux stability avoids generation of heat, and thus energy loss, and in addition discourages free-floating mechanisms from wobbling while suspended in the flux field.

Figure 1:
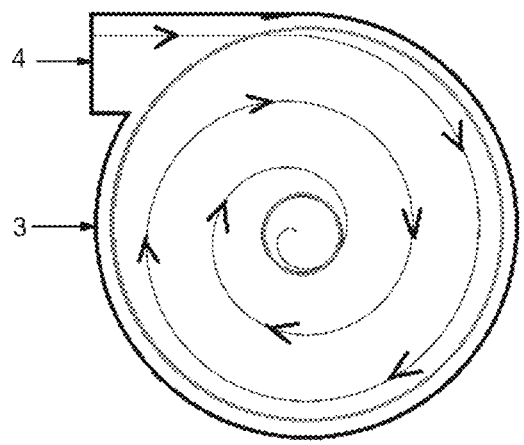
FIGS. 1 and 2 show top and side views, respectively, of one embodiment of a Tesla turbine configured for use in a hydrogen reclamator according to the present invention.
Figure 2:
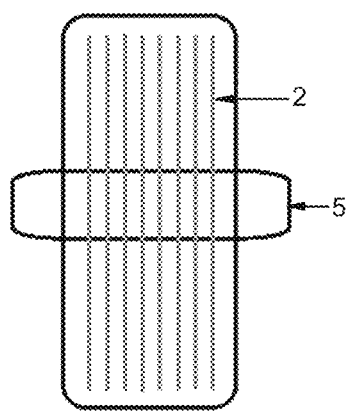

The development of a more efficient turbine has always been a consistent engineering challenge. Nikola Tesla devised a turbine that he claimed to be his favorite invention, but of all the great things he developed, his Tesla turbine has seen the least utilization. The reason Tesla had such high hopes for his turbine was because he discovered how to utilize the boundary-layer effect (the Coanda effect) to drive a rotor about an axis within an enclosed chamber 3 designed to contain the venturi forces built up through hot air or steam. This is illustrated in FIGS. 1 and 2. The Tesla turbine 1 has an inlet 4 to introduce matter into the chamber 3 and a rotor shaft 5 perpendicular to at least one rotor disc 2.

An astounding property of the Tesla turbine 1 is its ability to achieve extreme RPMs at high pressures. Tesla, however, was not able to realize the full potential of this design because the rotor discs 2 in his model would deform themselves due to the immense centrifugal forces acting upon the rotor at a compounding right angle. According to the present invention, there is potential to make the Tesla turbine 1 even more efficient while still utilizing the boundary-layer effect, while negating over acceleration of the rotor. It is possible to eliminate harmonic imbalances in the rotor discs by suspending the turbine axle and terminal rotor discs in space using electromagnetic flux. But even in the absence of stability provided by the electromagnetic flux, the Tesla turbine can still provide an ideal chemical reaction chamber with the added benefit of recapturing kinetic energy present in exhaust gas escaping a combustion motor.

The atmospheric force acting upon the rotor is expressed in the conjecture formula $P=tK-tC$, where $P$ is the net positive power, $t$ is time, $K$ being the compounding kinetic energy acting upon the rotor from the exhaust gasses of a combustion motor, and $C$ being the sum of the constant electrical current required to maintain flux levitation and electrolysis of water.

Further, it can be shown that $P$ is not only the net positive electrical current due to rotation of the turbine rotor, but also the summation of the stored energy potential within the newly reclaimed hydrocarbons being the physical byproduct of the hydrocarbon reclamator.

Said exhaust gasses travel along a vector resembling the Fibonacci sequence as they fall to the center of the turbine due to venturi forces, releasing their kinetic energy against the rotor discs as they do so. $K$ is a positive exponential function so long as the system continues to be fed with exhaust gasses. Because $K$ contains an irrational exponential function, and $C$ contains a fixed constant, given enough factor of $t$ time, $P$ will result in a net positive power output.

$$P=t(K)-t(C)$$

The Fibonacci sequence is obtained by taking the last two numbers in a series and adding them together.

$$t_0 \; t_1 \; t_2 \; t_3 \; t_4 \; t_5 \; t_6 \; t_7 \ldots$$

0 1 1 2 3 5 8 13 . . .

$$K = \infty$$

where K=positive infinity because K contains a compounding Fibonacci summation multiplied by time.

$$C = L + E$$

where L=total current to suspend rotor weight (unchanging) and E=total current to preform electrolysis (unchanging).

$$\infty - C = \infty$$

Figure 8:
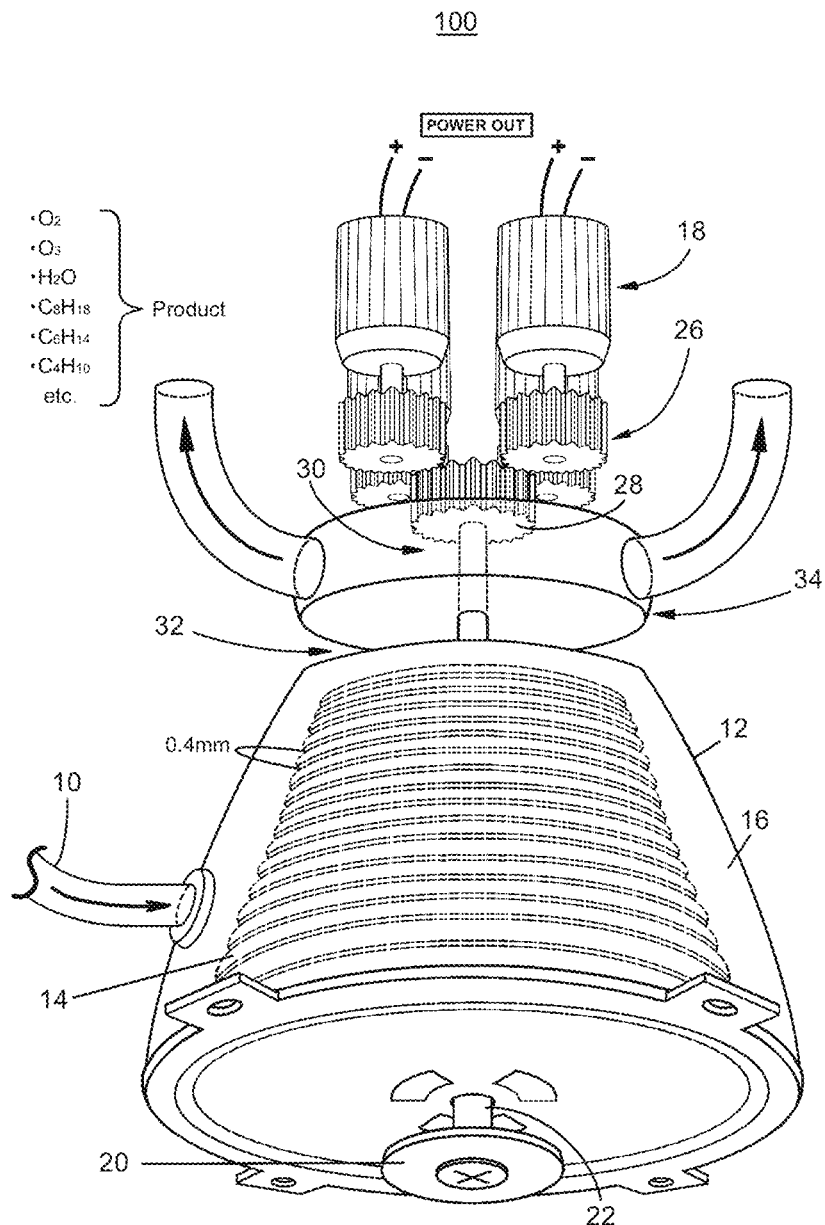
FIG. 8 is a perspective view of one embodiment according to the invention of a multi-disc Tesla turbine for use in a hydrocarbon reclamator.

In suspending a rotor via magnetic flux forces within a closed chamber, the resulting system will be a mechanically frictionless Tesla turbine. An early prototype of the hydrocarbon reclamator may function within a margin of efficiency without the use of a magnetic flux field, however, such an arrangement will lose the ability to draw oxygen away from the catalytic metals preforming Sabatier and Fischer-Tropsch reactions due to oxygen para-magnetism, and the repulsion of carbon from the flux fields due to the carbon diamagnetism. The kinetic energy built up within the exhaust 201 of an internal combustion engine 200 can be recaptured via this frictionless rotor 30. Affixed to the top of the flux suspended rotor 30 will be a gear 28 with teeth composed of permanent magnets. As shown in FIG. 8, the flux gear 28 affixed upon the top of the axle shaft 22 will free-float in close proximity to adjacent flux gears 26 affixed to the axles 32 of electric generators 18 for power reclamation. In this way, the kinetic force from the rotor 30 is directly transferred via flux forces, rather than physical friction. In a conventional Tesla turbine design, however, the use of a conventional brushless motor may be used to recover electrical energy from the turbine axle.

Figure 6:
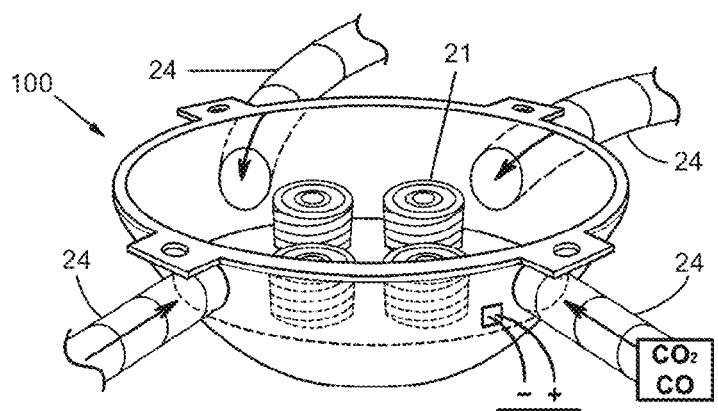
FIG. 6 is a perspective view of a diamagnetic structure used to generate a magnetic flux to enable near-frictionless rotation of a Tesla turbine in one embodiment of a hydrocarbon reclamator according to the invention.
Figure 7:
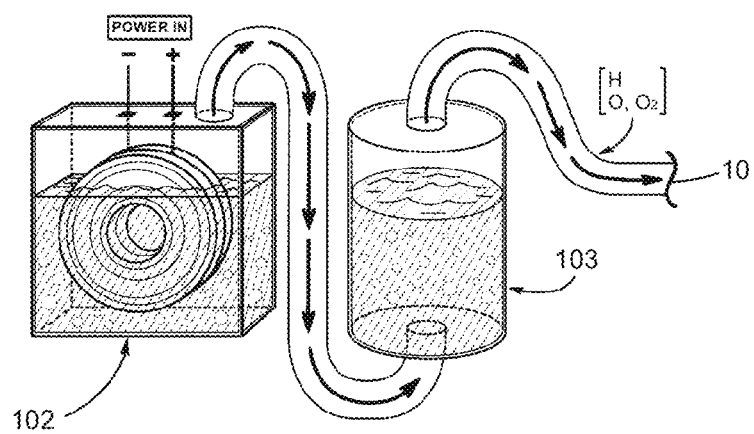
FIG. 7 is a perspective view of one embodiment of an electrolysis subsystem for generating hydrogen for supplying a hydrocarbon reclamator according to the invention.

There is an unfulfilled need for a high efficiency system for the recovery of kinetic energy stored within the expanding exhaust from an internal combustion engine. Current exhaust systems allow for otherwise unused energy to be lost to the atmosphere. By implementing a modified and modernized iteration of Tesla's turbine alongside utilization of the Fischer-Tropch processes, such a device will herein be referred to as the Hydrocarbon Reclamator 100, which is shown in FIGS. 6, 7 and 8. This mechanism functions to negate energy loss—and byproducts of combustion can be efficiently reclaimed.

A hydrogen reclamation system 100 of the present invention is a highly efficient system that benefits from the elimination of mechanical friction upon the mechanism receiving the kinetic energy transferred from expanding hot gasses. The elimination of friction upon the rotor may best be achieved by the implementation of flux force induction. By replacing large moving metallic parts with magnetic fields generated by the interaction of a permanently affixed magnet 20 with electromagnetic coils 21, the rotor 30 of the mechanism can achieve higher RPMs than conventional turbine systems while minimizing loss of energy via friction and torque instability.

The frictionless Tesla turbine employed in the present invention is important to carbon capture and hydrocarbon production because the energy required as input to the chemical process of creating hydrocarbons must be as efficient and free of any static restraints. Syngas may be created by multiple means such as introducing hydrogen at high pressures within the presence of carbon dioxide or carbon monoxide and a catalytic metal known to produce two possible catalytic reactions. These two reactions are firstly the Sabatier reaction, first discovered by French chemist Paul Sabatier and Jean-Baptiste Senderens in 1897. The Sabatier reaction utilizes a nickel catalyst to promote hydrogenation of carbon dioxide through an exothermic process which results in the conversion of one carbon dioxide molecule to be transformed in to one methane molecule and two water molecules. The second reaction is known as the Fischer-Tropsch process which was developed by Franz Fischer and Hans Tropsch at the Kaiser-Wilhelm-Institute in Mulheim an der Ruhr, Germany in 1925. The Fischer Tropsch process produces the same amount of exothermic output as the Sabatier reaction, a net joules of 165.0 kj/mol, but Fischer-Tropsch is best summarized as a continuation of the hydrogenation process resulting in the formation of longer hydrocarbon bonds. This results in the production of heavier hydrocarbons such as butane, propane, and even octane under optimal conditions. In one embodiment, Tesla turbine style rotors of the hydrocarbon reclamator will be constructed out of catalytic metals know to produce both the Sabatier reaction and the Fischer-Tropsch process. Nickle, iron, and aluminum have been verified as being viable catalysts for the Fischer-Tropsch process, though catalysts with less atomic mass tend to produce lighter-weight hydrocarbons—the use of a heavier catalyst such a ruthenium or cobalt may be used to facilitate the generation of larger hydrocarbons (e.g., heptane to octane), whereas nickel and iron may only be capable of producing smaller molecules (e.g., methane to butane).

The flux suspension array 20, 21 at the base of the rotor shaft 22 in practice provides slight ionization of the incoming 24 feed stock carbon dioxide, which is simultaneously providing flux induced levitation for the free-floating rotor 30, while hydrogen is introduced 10 to this ionized gas mixture. Hydrogen gas production is best facilitated within an electrolysis chamber 102 containing an electrolyte such as sodium hydroxide such as to lower the electrical resistance of the water 103 in order to promote more efficient hydrogen production. A model of such an electrolysis chamber 102 is shown in FIG. 7. The hydrogen is then plumbed 10 directly into the housing 12 of the hydrocarbon reclamator 100, where it meets with the carbon dioxide, plumbed in through an exhaust intake 24, and catalytic metals. See FIGS. 6 and 8. With the inner walls 16 of the turbine housing 12, which are plated in nickel, hydrocarbon fuel production will take place due to Sabatier reaction. After methanation takes place via Sabatier reaction at the turbine housing 12 inner walls 16, the methane gas serves to promote the Fischer-Tropsch process by pre-methanation of the hydrocarbons that will become longer hydrocarbon chains by interacting with the heavier catalytic metals of the turbine rotor discs 14 that are shown in FIG. 8.

Figure 4:
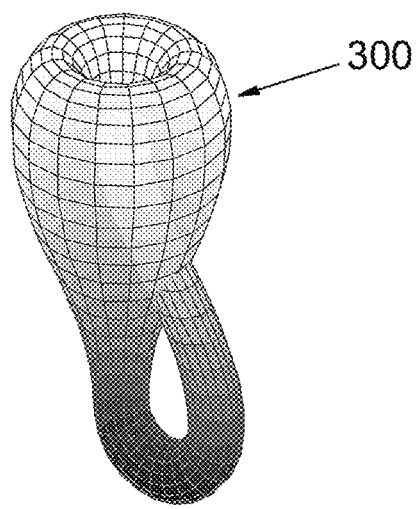
FIG. 4 is a diagram of a topographical shape known as a Klein bottle.
Figure 5:
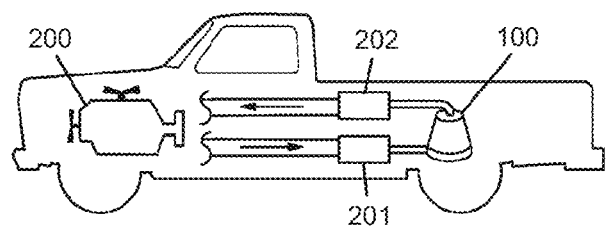
FIG. 5 shows a typical power generation system, in the form of a vehicle having an internal combustion engine, that burns hydrocarbon fuels and emits unburnt hydrocarbons into the atmosphere.

The present design for a hydrocarbon reclamator 100 takes advantage of the flow rate of exhaust gasses and feeds that energy into a chemical process that converts the exhaust back into a stable hydrocarbon. The exhaust produced by standard combustion engines 200 such as depicted in FIG. 4, drives the frictionless Tesla turbine to RPMs sufficient to create an electrical current that may be generated by reclamation generators 18 shown at the top of the structure in FIG. 9. The frictionless rotor 30 is composed of a permanent magnet 20 at the base of the rotor, which interacts with electromagnetic coils 21, and extends a vertical shaft 22 containing multiple Tesla turbine disc plates 14 stacked in sequence as shown in FIG. 8. These disc plates 14 can be further stabilized by a permanent diamagnetic housing containing a material such as Bismuth or perhaps even a super-conductive material with diamagnetic properties. This will ensure that the rotor maintains optimal stabilization while the Coanda effect spins the rotor 30 about its axis at the boundary layer effect junction 32. These discs 14 may contain an even arrangement of flow holes adjacent to an odd arrangement of flow holes about the rotor housing. The discs 14 never contact the rotor housing 12, but the boundary-layer effect still applies as the rotor 30 rotates within the reclamator housing.

Figure 3:
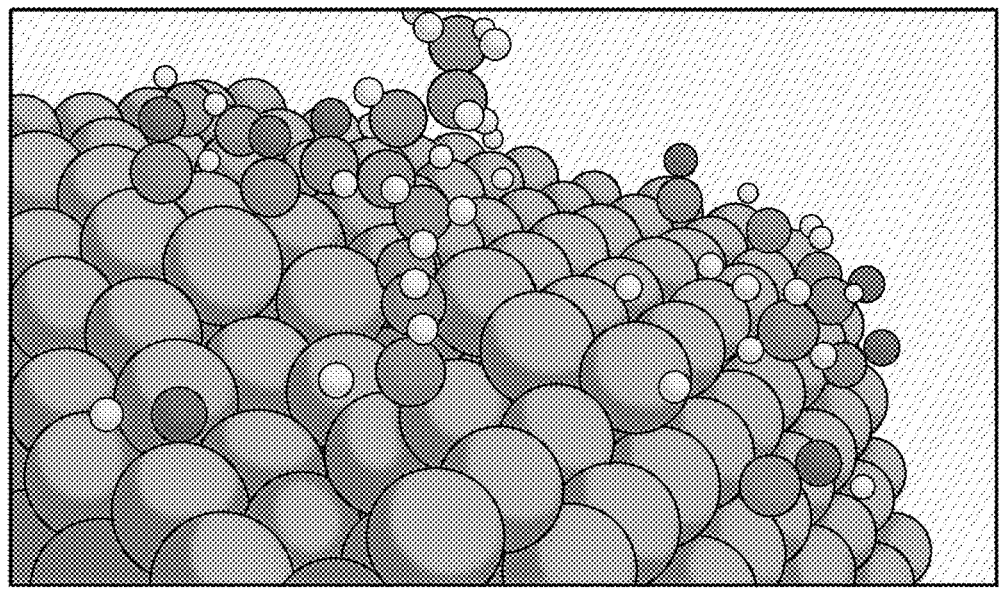
FIG. 3 is a molecular model illustrating a binding reaction that occurs when introducing hydrogen and carbon to a catalytic metal.

The energy recovered from the rotational motion of the rotor will be back-fed into the circuit of flux-field generation, electrolysis, and ionization of the feed stock carbon dioxide. This newly produced hydrocarbon material can then be captured, stored, and reburned to create a prolonged energy lifecycle. The new hydrocarbons pass through a hydrocarbon compressor intake manifold 34 of a fuel compressor 202 prior to being reintroduced to the internal combustion engine 200. The flow path of the involved atmosphere forms a topographical shape mathematicians would refer to as a Klein Bottle 300, as depicted in FIG. 3. The internal combustion engine 200 when equipped with a hydrocarbon reclamator 100 is able to rebreath its spent exhaust because the exhaust has been rehydrated, eliminating the need to expel carbon into the atmosphere.

A hydrogen reclamation system 100 according to the invention recycles input kinetic energy and captures it in the form of a returnable fuel by using the exhaust byproduct as a feed. The invention advantageously utilizes a unique combination of known phenomenon to recycle carbon into form reusable hydrocarbons rather than losing it to the atmosphere. Any internal combustion engine 200 that produces carbon dioxide and carbon monoxide gas can be retrofitted with a hydrocarbon reclamator 100 of the appropriate size and scale to mitigate the effects of harmful byproducts of fuel combustion and simultaneously increase overall energy efficiency.

Exemplary embodiments of the invention have been disclosed in an illustrative style. Accordingly, the terminology employed throughout should be read in a non-limiting manner. Although minor modifications to the teachings herein will occur to those well versed in the art, it shall be understood that what is intended to be circumscribed within the scope of the patent warranted hereon are all such embodiments that reasonably fall within the scope of the advancement to the art hereby contributed, and that that scope shall not be restricted, except in light of the appended claims and their equivalents.

I claim:

1. A hydrocarbon reclamator, comprising:
   a closed chamber having an exhaust inlet port, a hydrogen inlet port, and a hydrocarbon outlet port;
   a means for generating a magnetic flux at the base of the closed chamber; and
   a rotor suspended by the magnetic flux within the closed chamber, the rotor having a surface having a catalyst, the rotor configured to direct gas from the inlet ports to the outlet port;
   whereby hydrogen entering the closed chamber via the hydrogen inlet port combines with carbon entering the chamber via the exhaust inlet port to form a hydrocarbon that exits the closed chamber via the hydrocarbon outlet port.

2. The hydrocarbon reclamator of claim 1, wherein a base of portion of the rotor comprises a permanent magnet.

3. The hydrocarbon reclamator of claim 1, configured to generate hydrocarbons by the Fischer-Tropsch process.

4. The hydrocarbon reclamator of claim 1, further comprising an electrolysis subsystem configured to generate and deliver the hydrogen to the hydrogen inlet port.

5. The hydrocarbon reclamator of claim 1, wherein the exhaust inlet port and the hydrocarbon outlet port are in fluid communication with a combustion chamber of an internal combustion engine.

6. The hydrocarbon reclamator of claim 1, wherein the means for generating the magnetic flux comprises one or more electrical coils.

7. The hydrocarbon reclamator of claim 1, wherein the rotor comprises a Tesla turbine having a plurality of discs concentrically mounted on a central shaft of the rotor and spaced apart axially along the shaft, the rotor configured so that gasses entering the chamber via the exhaust inlet port travel toward a center of the rotor due to venturi forces to release kinetic energy against one or more of the discs.

8. The hydrocarbon reclamator of claim 1, wherein the catalyst comprises a metal plated on a surface of the rotor.

9. The hydrocarbon reclamator of claim 8, wherein the catalyst is selected from the group consisting of ruthenium, platinum, nickel, and iron.

10. The hydrocarbon reclamator of claim 1, wherein the rotor is configured to generate electrical current in response to exhaust gas entering the exhaust inlet port.

11. The hydrocarbon reclamator of claim 10, further comprising an electrolysis subsystem configured to generate and deliver the hydrogen to the hydrogen inlet port, wherein the electrolysis subsystem is electrically powered by the electrical current generated by the rotor.

12. The hydrocarbon reclamator of claim 10, wherein the means for generating a magnetic flux at the base of the closed chamber is electrically powered by the electrical current generated by the rotor.

13. The hydrocarbon reclamator of claim 1, further comprising a primary magnetic flux gear affixed atop the rotor.

14. The hydrocarbon reclamator of claim 13, wherein the primary magnetic flux gear includes one or more gear teeth comprising a permanent magnet.

15. The hydrocarbon reclamator of claim 13, further comprising one or more secondary magnetic flux gears magnetically coupled to the primary magnetic flux gear.

16. The hydrocarbon reclamator of claim 15, wherein the one or more secondary magnetic flux gears are configured to generate electrical current in response to rotation of the primary magnetic flux gear.

17. The hydrocarbon reclamator of claim 1, wherein the rotor comprises a Tesla turbine.

18. The hydrocarbon reclamator of claim 17, wherein the Tesla turbine comprises a plurality of rotor discs and wherein the catalyst is formed on one or more surfaces of the rotor discs.

19. The hydrocarbon reclamator of claim 18, wherein each of the plurality of rotor discs defines one or more flow holes configured to direct gas from the inlet ports to the outlet port.

20. The hydrocarbon reclamator of claim 18, wherein at least one of the rotor discs comprises a material having diamagnetic properties.

* * * * *